United States Patent
Lojkowski et al.

(10) Patent No.: US 7,888,658 B2
(45) Date of Patent: Feb. 15, 2011

(54) ZIRCONIUM DIOXIDE LUMINESCENCE OXYGEN SENSOR

(75) Inventors: Witold Lojkowski, Warsaw (PL); Donats Millers, Riga (LV); Janusz Fidelus, Mucharz (PL); Larisa Grigorieva, Riga (LV); Agnieszka Opalinska, Zyraτdow (PL); Urszula Narkiewicz, Szczecin (PL); Wieslaw Strek, Wroclaw (PL)

(73) Assignee: Instytut Wysokich Cisnien Polskiej Akademii Nauk, Warsaw (PL)

( * ) Notice: Subject to any disclaimer, the term of this patent is extended or adjusted under 35 U.S.C. 154(b) by 256 days.

(21) Appl. No.: 11/991,487

(22) PCT Filed: Sep. 1, 2006

(86) PCT No.: PCT/PL2006/000060

§ 371 (c)(1),
(2), (4) Date: May 22, 2008

(87) PCT Pub. No.: WO2007/027116

PCT Pub. Date: Mar. 8, 2007

(65) Prior Publication Data

US 2009/0256083 A1 Oct. 15, 2009

(30) Foreign Application Priority Data

Sep. 1, 2005 (PL) .................................. 376856

(51) Int. Cl.
*G01J 1/58* (2006.01)

(52) U.S. Cl. .................................................. 250/459.1
(58) Field of Classification Search ............. 250/252.1, 250/459.1, 573

See application file for complete search history.

(56) References Cited

U.S. PATENT DOCUMENTS 5,030,420 A * 7/1991 Bacon et al. ............. 422/82.07
6,815,211 B1 11/2004 Blazewicz et al.

FOREIGN PATENT DOCUMENTS

WO WO03040727 5/2003

* cited by examiner

*Primary Examiner*—David P Porta
*Assistant Examiner*—Marcus H Taningco
(74) *Attorney, Agent, or Firm*—Horst M. Kasper

(57) ABSTRACT

A method of measuring oxygen partial pressure in gases, such as hot engine exhaust gases, uses a calibrated luminescence sensor and comprises the steps of bringing nanocrystalline zirconium dioxide $ZrO_2$ (2) in said sensor into contact with a gas to be measured, illuminating the zirconium dioxide with a UV-VIS light pulse emitted from a light source (3) and adapted to induce luminescence of the zirconium dioxide, registering the time dependence of the luminescence intensity of the $ZrO_2$ using a photodetector (4) and a recorder (5), determining a particular intensity, e.g., the maximum intensity of the registered luminescence pulse, and comparing said determined intensity with calibration data of the luminescence intensity as a function of oxygen partial pressure for the sensor temperature at the time of the measurement.

15 Claims, 3 Drawing Sheets

ZIRCONIUM DIOXIDE LUMINESCENCE OXYGEN SENSOR

TECHNICAL FIELD

The invention relates to method of measuring of partial pressure of oxygen in gases by measuring the excited luminescence of the sensor, especially applicable in the measurements of the oxygen amount in exhaust gases of car engines as well as in the control of technological processes, control of the oxygen level in glasshouses, lecture rooms, conference rooms, restaurants and in the optimization of combustion processes as well as in metallurgy.

BACKGROUND ART

The patent PL 142779 discloses a device for the constant measurement of the oxygen amount in hot gases, based on a method of the use of heat of catalytic reaction of oxygen with hydrogen, while from the U.S. Pat. No. 3,849,539 a method is known for marking and deoxygenation from an inert gas stream with regard to hydrogen.

The method of measurement in accordance with the U.S. Pat. No. 3,849,539 cannot be used to determine the oxygen level directly in hot gases in view of the necessity of the initial and exact dry of the analyzed gas. Furthermore, the concentration of oxygen in the analysed gas must be less than 1% of the gravimetrical.

Emission and use of fuel control systems, consisting of three-way catalytic converters (TWC) using potentiometric oxygen sensors based on zirconium dioxide as well as amperometric sensors with linear lambda control based on zirconium dioxide ($\lambda=1$) are also known [E. Ivers-Tiffee, K. H. Hardtl, W. Menesklou, J. Riegel, Principles of solid state oxygen sensors for lean combustion gas control, Electrochimica Acta 47 (2001) 807-814]. The principle of operation of the above-mentioned sensors is connected with the electric current conduction, what is disadvantageous to certain solutions.

Solutions most closely related to the subject of the invention have been disclosed in U.S. Pat. No. 6,815,211 and publication US 2001031224 A1. In those solutions the devices made of systems, which on the basis of the signal from the quenching of luminescence provide information about the oxygen concentration in analysed gases, are described. The elements of those systems include:

(a) a device delivering measured gases, sensor sample chamber, in which the luminescence is being excited, and the fading time of which reflects the concentration of oxygen in gases; (b) a converter equipped with the source of light for the stimulation of the compound capable of luminescence in the sensor and sensitive light detector for the processing of emitted energy from the luminescent compound during the luminescence decay, which is being processed in the electric signal indicating the oxygen concentration in monitored gases, and (c) subsystems for the keeping of constant temperature of the sensor and processing of signal generated by the sensitive light detector. The disadvantage of the above-described solutions is complex structure.

The method of monitoring the oxygen concentration disclosed in U.S. Pat. No. 6,815,211, consists of the following stages: (a) formation of the solution composition showing luminescence in the organic solvent; (b) swelling of the matrix consisting of the hydrophobic polymer film containing large amount of the open micropores, (c) introduction of the solution composition showing luminescence to the film by its penetration inside the swollen film; (d) removal of the organic solvent in such a way, so that during the shrinkage, the microporous, hydrophobic polymer will trap at least half of the composition showing luminescence.

In the Paragraph 20 of U.S. Pat. No. 0,031,224, has been described an oxygen sensor from the zirconium oxide, in which the amount of oxygen is determined by the use of the ionic conductance. The solution similar to the subject of the invention is being also represented by the optical, fluorescent oxygen detector named "Rugged D.O." (http://www.in-situ.com/In-Situ/Products/MPTROLL9000/TROLL9000_RDO.html), which enables the detection of oxygen concentration dissolved in aqueous solutions. The monitoring method is based on the fact, that the sensitive element of the detector (luminophore) is being activated and stimulated by the source of the blue light (e.g. UV LED). The detector element, which is being stimulated in this way, emits a red light of the intensity inversely proportional to the current oxygen concentration in water. Also the time length of the decay between the maximal blue light value and the maximal value of the response of the fluorescent red light is inversely proportional to the concentration of the present oxygen. The time of the decay can be expressed as a phase displacement between the incident blue light and the fluorescent red light.

DISCLOSURE OF INVENTION

The goal of this invention is to provide a method of the measurement of the partial pressure of oxygen in gases by the way of measurement of excited luminescence of the sensor material.

This goal has been achieved by the method, in which nanocrystalline zirconium dioxide in the calibrated sensor is contacted with the measured gas and is illuminated by an UV light impulse, which induce luminescence of the zirconium dioxide. Then the luminescence intensity time dependence is being registered, the luminescence intensity of pulse is being determined and the result obtained is compared with the calibration results of the luminescence intensity in the function of the partial pressure oxygen for the sensor temperature at a given time.

In the method determined luminescence intensity can equal maxima of luminescence response pulse.

In one variety of the invention the sensor contains nanocrystalline zirconium dioxide with crystallites from 3 nm to 200 nm made of monoclinic phase, doped tetragonal phase, regular doped phase or the mixture of those phases.

In another varieties of the invention the zirconia contains ions known to stabilise the monoclinic, tetragonal or regular phases or their mixtures or the zirconia contains ions of rare and transition metals, which improve the sensitivity of the sensor and decrease the operating temperature.

In another variety of the invention when the temperature of the measured gas is below 100° C., the sensor is heated to a temperature in the range of 100° C. to 900° C. and the sensor working temperature is proportional to the size of the nanocrystalline grains.

Wavelength of the used inducing excitation light impulse can be within the range from 210 nm to 620 nm.

In another variety of the invention the measuring of the sensor temperature at a given time is made on the basis of the exponent of the exponential function describing the luminescence decay as well as comparing the obtained value with the calibration results determining the connection between the temperature and this exponent.

In yet anther variety measuring of the sensor temperature at a given time is made on the basis of the rate of decay of luminescence, which is characteristic for the given material used in the sensor.

For the purpose of the invention the determined luminescence intensity can also equal any fixed level of luminescence response pulse which is lover than maximum level.

The invention enables the simultaneous measurement of the oxygen amount in gases and the sensor temperature, what eliminates the necessity to stabilize the temperature and use of a temperature control device. The sensor working temperature can be regulated by the selection of the size of the nanocrystalline grains $ZrO_2$ and in case of the use of small zirconium oxide crystals the sensor can work in temperatures above 100° C. The invention enables the determination of the amount of oxygen in hot gases as well as the determination of temperature of those gases. Furthermore, the way of measurement in accordance with the invention, is characterized by clear algorithm and relatively simple measurement data handling. In case of the luminescent sensor $ZrO_2$ of the tetragonal phase, on account of low electric conduction, the heating element can be placed directly on $ZrO_2$ by the method of the thin film settlement. In the measurement method, the performance of only two measurements in one stimulated cycle, in order to determine the partial pressure of oxygen in gas and the sensor temperature, is required.

BRIEF DESCRIPTION OF DRAWINGS

The object of the invention has been schematically presented on the picture, where.

MODE FOR CARRYING OUT INVENTION

Figure 1:
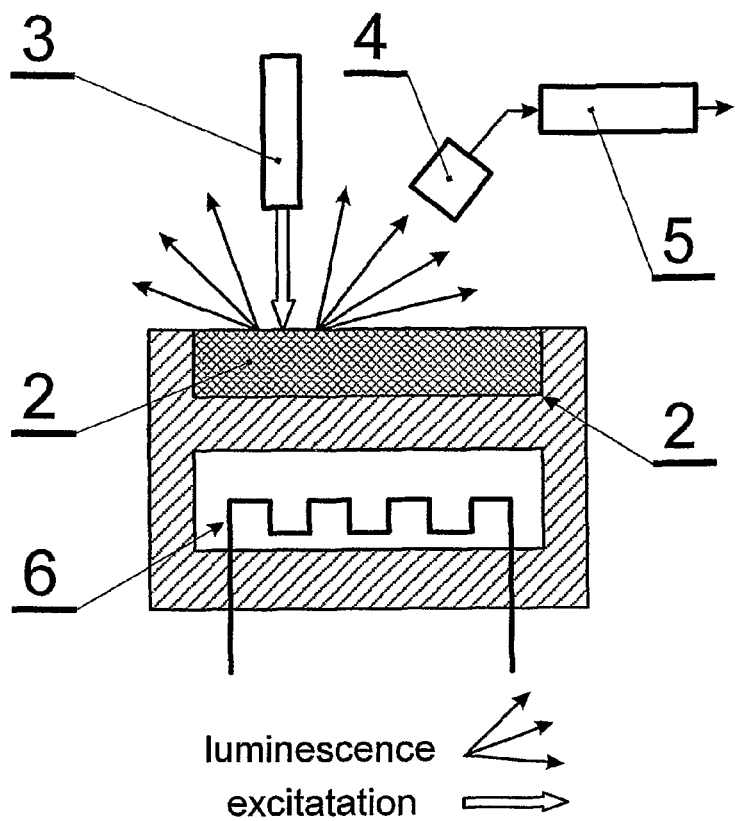
FIG. 1 shows a scheme of the system for the measurement of oxygen level in gas atmosphere and the sensor temperature.

The invention will be described in detail on the basis of the examples of its realization presented below. The exemplary scheme of the system for measuring the partial pressure of oxygen in gas atmosphere and the sensor temperature (FIG. 1), equipped with a heating element 6 that heats up the sensor material 2 placed in the chamber 1 is characterised in that the sensor material contains $ZrO_2$ of a monoclinic phase, doped tetragonal phase, regular doped phase or mixture of those phases. The sensor material can work in various temperature ranges depending on the selection of the size of the nanocrystalline grains $ZrO_2$. The sensor is also equipped with an excitation light source 3, photodetector 4 and recorder 5. According to the invention, the light from the pulsing source 3 excites the own luminescence in $ZrO_2$ (2). The luminescent light is being detected by the photodetector 4, and afterwards the intensity and the time of the luminescence decay 5 are being registered.

The luminescence intensity and the time of its decay provide information about the oxygen partial pressure (in the demanded temperature $ZrO_2$) and about the temperature itself. From this point on, the temperature can be determined during every measurement of the luminescence, what eliminates the necessity to use an additional device for stabilization and control of the temperature.

Figure 2:
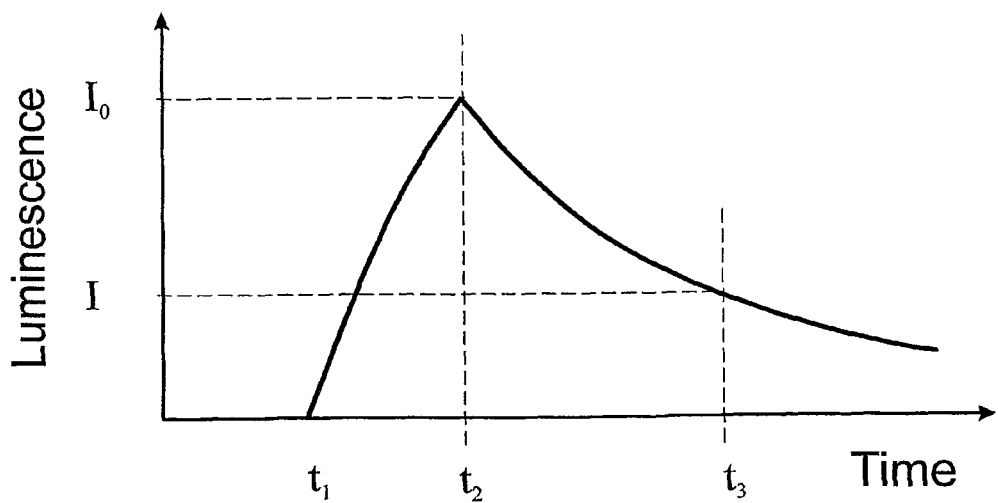
FIG. 2 shows the possible order of operations and measurements in the time function.

The possible order of operations and measurements in the time function is presented on FIG. 2. The picture shows the situation after switching on the heating element 6 and current of constant value properly chosen depending on the size of the nanocrystallines $ZrO_2$. After the equal time $t_1$, the resistance heated zirconium dioxide reaches constant temperature proper for the used size of the nanocrystallines $ZrO_2$, an excitation pulse sent by the excitation light source 3 is being activated. The duration time of the excitation pulse is $t_2-t_1$. The luminescent light is being detected by the photodetector 4 and the intensity as well as the luminescence decay time are being registered by the recorder 5. The luminescence response amplitude $I_0$ presented on the FIG. 2 depends on the oxygen amount in $ZrO_2$. According to the FIG. 2 the luminescence response reaches its maximum at the end of the excitation pulse $t_2$. The luminescence decay time equal $t_3-t_2$ is being defined as a time, after which the luminescence intensity decreases by the factor $1/e$; ($I_0/I=e$, where $\log_e e=1$). According to the FIG. 2 the excitation time must be shorter than (constant) luminescence decay time ($t_3-t_2$), the quantity of which is being also determined by the maximum frequency repetition of the excitation.

Figures 3A, 3B:
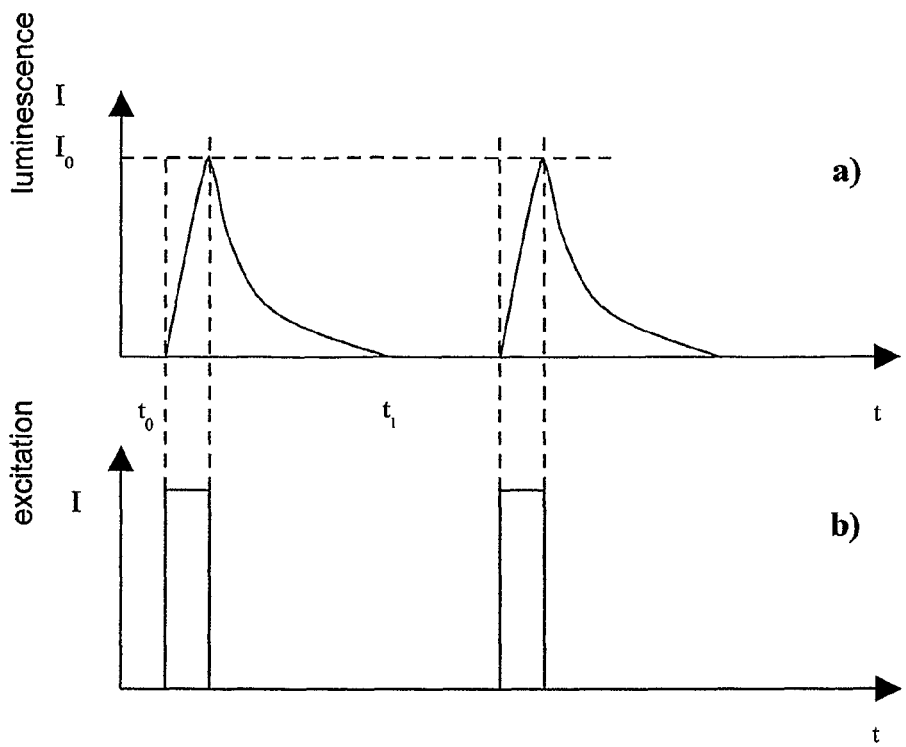
FIG. 3a and FIG. 3b present a type of correct value evaluation of the intensity amplitude of the luminescence ($I_0$), by the help of which one can determine the amount of oxygen in measured gas.

The intensity of the luminescence light $ZrO_2$ is a parameter determining the oxygen amount, so the accuracy of the oxygen amount measurement depends mainly on the accuracy of its measurement. However there is an additional light that may increase the detection fault. This light is composed of: (a) light scattered in the apparatus; (b) background from the previous luminescence; and (c) scattered excitation light. The average scattering measurements for the luminescent measurements $ZrO_2$ are in the range 1-5%. Therefore the scattered light detected by the photodiode must be less than 5%. The scattered excitation light can be removed for example by the spectral selection with the use of proper filters, while the scattered light in the apparatus (light from the environment of a detector) may be reduced by a proper construction of the detector, so the dominant problem remains the light resulting from the background after the previous luminescence. If the excitation pulses (FIG. 3b) follow each other in time intervals that are long enough, the decay of the luminescence background (FIG. 3a) can be very good. In the time interval $\Delta t=t_1-t_0$ (FIG. 3b), the luminescence decay time is actually shorter than the boundary value of the photodiode, so the measurement $I_0$ is a good parameter for the oxygen concentration measurements.

Figures 3C, 3D:
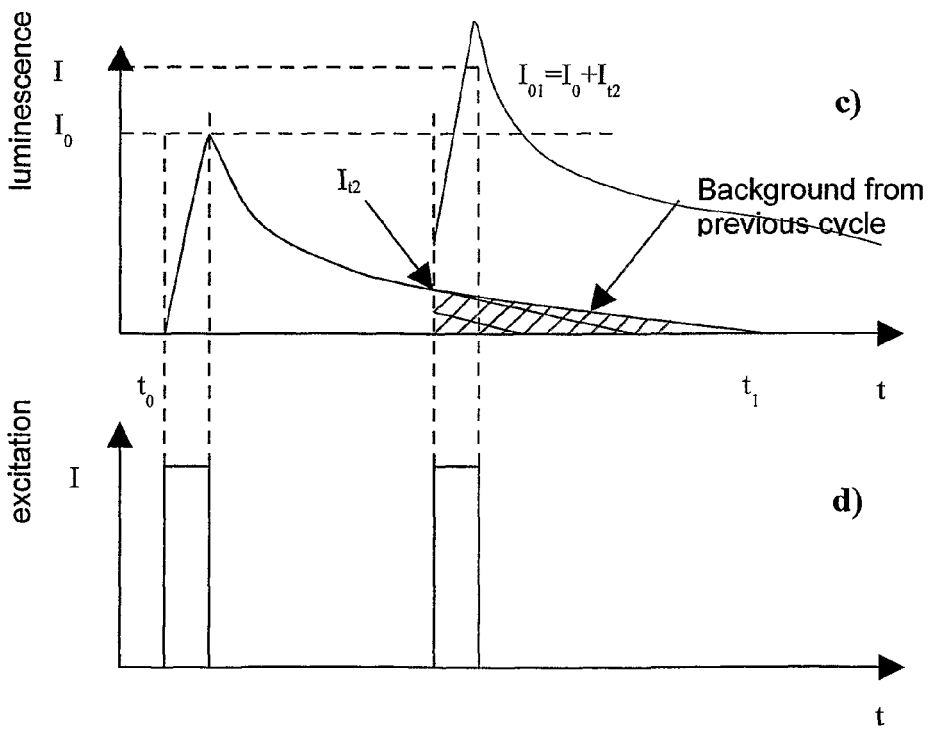
FIG. 3c and FIG. 3d present a method of measurement, in which the designated amplitude value of the luminescence intensity ($I_{01}$) is overestimated due to the quicker turning on of another pulse in time ($t_2$), which corresponds with the luminescence intensity ($I_{t2}$)

The crucial issue is the highest frequency of the excitation. If the subsequent excitation pulse is within the range $t_1-t_0$ (FIGS. 3c and 3d), the photodiode will register the value $I_{01}$, which consists of $I_0$ and a background from the previous excitation causing luminescence $I_{t2}$ (FIG. 3c). Therefore, the measurement $I_{01}=I_0+I_{t2}$ is not proper for the determination of the oxygen concentration. The following calculations can be made:

The constant time of the luminescence decay is determined by the expression (A):

$$I = I_0 \exp\left(-\frac{t}{\tau}\right), \quad (A)$$

and after transformation:

$$\frac{I}{I_0} = \exp\left(-\frac{t}{\tau}\right)$$

If the boundary of the luminescent measurements of the scattering is 5%, then:

$$\frac{I}{I_0} = 0,05 \text{ or } \exp\left(-\frac{t}{\tau}\right) = 0,05$$

what gives $t \approx 3\tau$;

However, if the boundary would be 1% then:

$$\frac{I}{I_0} = 0,01 \text{ or } \exp\left(-\frac{t}{\tau}\right) = 0,01$$

what gives $t \approx 4.6\tau$,

Therefore when the time interval between the pulses is $\Delta t \approx 4\tau$, one gets the high enough value accuracy of the measurement of the light intensity, where the fault from the background of the luminescence is approx. 1%.

Therefore, according to FIG. 2, the subsequent pulse should be introduced after the time not shorter than equal to the sum of excitation pulses ending time ($t_2$) and the quadruple of the luminescence time decay ($t_3-t_2$).

By the determination of the intensity of the excitation luminescence (own $ZrO_2$) as well as the time of its decay, the partial pressure of oxygen and the detector temperature are being determined. Of course both of the parameters require calibration.

Figure 4:
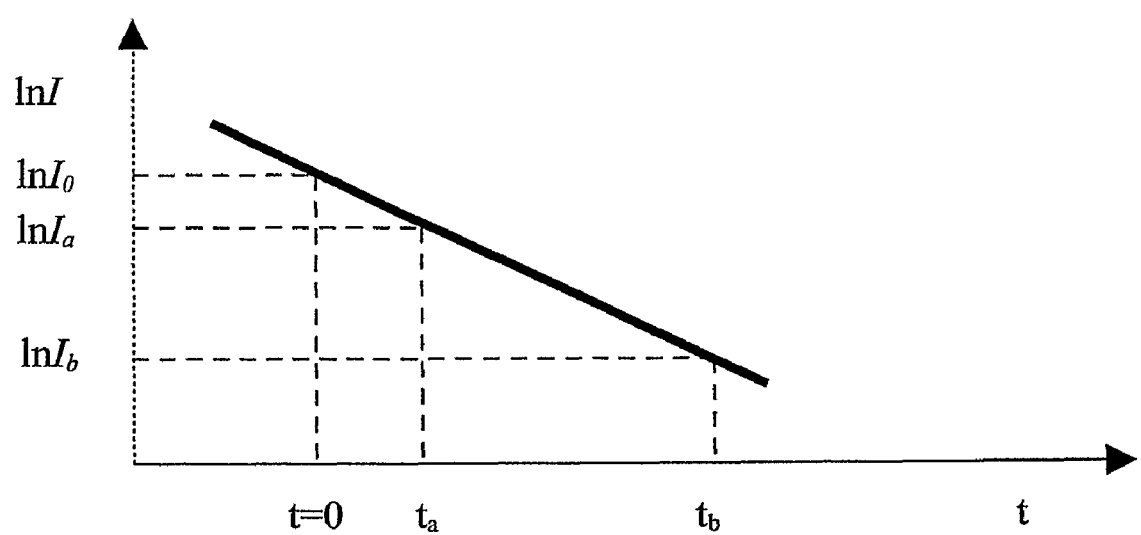
FIG. 4 depicts a method of a simultaneous measurement of the partial pressure of oxygen in gas and the sensor temperature.

The method according to the invention is described on the basis of the diagram on FIG. 4. According to the FIG. 4 the luminescence intensity measurement was made for two (at least) times ($t_a$, $t_b$). The luminescence intensity dependence from the time of its decay is represented by the following rule:

$$I = I_0 \exp\left(-\frac{t}{\tau}\right), \quad (A)$$

where: $I_0$ is initial luminescence intensity (in t=0) and I is luminescence intensity for every t.

After the transformation of the expression (A) we get the equation:

$$\ln I_a - \ln I_b = \frac{t_b - t_a}{\tau} \quad (B)$$

the diagram of which is a straight line (FIG. 4).

After the transformation of the equation (B), the luminescence decay time is:

$$\tau = \frac{t_b - t_a}{\ln I_a - \ln I_b} \quad (C)$$

From the equation (A) results that if t=0 then I=$I_0$, so the intersection point of the line representing the equation (B) with the line parallel to the axis ln(I) for t=0 determines the exact level $I_0$ and the accurate measurement of the maximum of the luminescence decay is not needed. The $I_0$ value is dependent on the initial oxygen amount in $ZrO_2$.

The measurements of the thermal energy of the luminescence activation decay ($E_a$) are being determined on the basis of the dependence of the luminescence decay time from the temperature, which is represented by the following formula:

$$\frac{1}{\tau} = \frac{1}{\tau_0} \exp\left(-\frac{E_a}{kT}\right) \quad (D)$$

where: $\tau$ is time constant of the luminescence decay, $1/\tau_0$ is preexponential factor, $E_a$ is thermal activation energy of the luminescence quenching, k is Boltzmann constant and T is temperature (in kelvins).

If the time constant of the luminescence decay ($\tau$) is determined for at least two different temperatures ($T_1$, $T_2$), then we can calculate $E_a$ and $1/\tau_0$.

By the proper transformation of the equation (D), the thermal energy of the luminescence activation decay can be calculated from the following equation:

$$E_a = K \frac{\ln \tau_1 - \ln \tau_2}{\frac{1}{T_2} - \frac{1}{T_1}} \quad (E)$$

The parameter $E_a$ must be determined before the first use for every detector and does not change during the work of the detector.

After the transformation of the equation (D), we may determine the temperature by using the following formula:

$$T = \frac{E_a}{K(\ln \tau_0 - \ln \tau)} \quad (F)$$

The luminescence intensity measurements (measured for the energy 2.65 eV) for $ZrO_2$ (consisting of the mixture of monoclinic and tetragonal phases) in the function of the partial pressure of oxygen in the gas mixture surrounding the material, have revealed the dependence of the quantity of the luminescence intensity of the zirconium dioxide from the oxygen amount in the surrounding gas mixture. Even minor differences in the partial pressure of oxygen (0.1%) were manifested by the change of the luminescence intensity. The obtained results have been gathered in the table 1, which shows the value of the signal of the luminescence intensity $ZrO_2$ for various oxygen partial pressures from the surrounding gas mixture (oxygen and nitrogen). The work temperature $ZrO_2$, consisting of the monoclinic phase of an average-sized grain having 24 nm and of tetragonal phase of an average-sized grain of 19 nm was 340° C.

| Partial pressure of oxygen [%] | Luminescence intensity |
|---|---|
| 9.7 | 19055 |
| 9.8 | 17800 |
| 21.7 | 14799 |

According to the invention, the subject obtained does not require temperature stabilization with high accuracy, so the temperature stabilization element and additional temperature sensor are not required. It results from the fact that every measurement contains data for the precisely defined temperature hence a special temperature sensor is no longer needed (Of course the prior calibration of the sensor material of a specific size of the grain in order to determine the proper temperature work range, is necessary).

The advantage of the luminescent oxygen sensor is a clear algorithm and relatively simple measurement data handling as well as the possibility of a simultaneous measurement of the oxygen amount in an analysed gas and the temperature of the detector.

In case of the luminescent detector $ZrO_2$ of a tetragonal phase, due to the low electric conduction, the heating element may be placed directly on $ZrO_2$ by the method of the thin film settlement.

Example 1

A measuring sensor 2 containing nanocrystalline zirconium dioxide, consisting of a stabilized tetragonal phase with an average size of crystallines 80 nm has been prepared, its calibration has been conducted, during which one has determined the thermal energy activation of the luminescence decay ($E_a$), parameter $\tau_0$, range of its work temperature, dependence of the luminescence intensity in the function of the oxygen pressure in this temperature range as well as the time of the luminescence decay in the temperature function, and then it has been placed in the sensor element containing metal chamber 1 and heated up to the temperature of 450° C. and the car exhaust fumes have been let in. Next, in time $t_0$, the surface of the sensor contacting the measured gas has been illuminated by the inducing UV light pulse with LED 3 (280 nm), which excited the own luminescence in $ZrO_2$ in the band 2.7 eV, which then was detected by the photodiode 4 (FDS 100) having signal rise—time 10 ns. The signal from the photodiode 4 was intensified by a wide-band amplifier, not presented on the drawing, of a band-width 440 MHz and the intensity (I) as well as luminescence decay time ($t_3-t_2$, FIG. 2) registered by a fast operating eight-bit analog-to-digital converter 5 and after the conversion sent to the data displaying module. The measurements of the above parameters were made in such a way, that after reaching maximum by the luminescence, two additional measurements of the luminescence intensity were made: $I_a$ for time $t_a$ and $I_b$ for time $t_b$, next the luminescence decay time was determined ($\tau$) as a difference quotient of the said measurement times ($t_b-t_a$) and the difference of the natural logarithms calculated during those luminescence intensity times ($\ln I_a-\ln I_b$) and in addition, one calculated the luminescence amplitude excited either for maxima by drawing through the two above-mentioned points a straight line, which intersection point with the line parallel to the axis InI crossing the point $t_0$ (LED flash point) determined the exact $I_0$ level, which is dependent on the initial oxygen amount in $ZrO_2$, either for other fixed level (e.g. half-height or other in accordance with calibration table formation requests). This value was compared with the value in the calibration table I=f (oxygen pressure) in the given temperature and the partial pressure of oxygen was obtained. The sensor temperature was determined as a quotient of the thermal energy of the luminescence activation decay ($E_a$) by the product of the Boltzmann constant (k) and the difference of the natural algorithm of the calibration parameter $\tau_0$ and the natural algorithm of the luminescence decay time determined earlier ($\tau$). Another excitation pulses were switched on after the time equal to the sum of the excitation pulses ending times ($t_2$) and the quadruple of the luminescence time decay ($t_3-t_2$).

Example 2

A measuring sensor 2 containing nanocrystalline zirconium dioxide, consisting of a stabilized tetragonal phase with an average size of crystallines 15 nm has been prepared, its calibration has been conducted, during which one has determined the thermal energy activation of the luminescence decay ($E_a$), parameter $\tau_0$ range of its work temperature, dependence of the luminescence intensity in the function of the oxygen pressure in this temperature range as well as the time of the luminescence decay in the temperature function, and then it has been placed in the sensor element containing metal chamber 1 and heated up to the temperature of 200° C. and the analysed gas (mixture of nitrogen and oxygen) has been let in. Next in time $t_0$, the surface of the sensor contacting the measured gas has been illuminated by the inducing UV light pulse with LED 3 (280 nm), which excited the own luminescence in $ZrO_2$ in the band 2.7 eV, which then was detected by the photodiode 4 (FDS 100) of the growth time 20 ns. The signal from the photodiode 4 was intensified by a wide-band amplifier, not presented on the picture, of a 440 MHz band-width and the intensity (I) as well as luminescence decay time ($t_3-t_2$) (FIG. 2) registered by a fast operating eight-bit analog-to-digital converter 5 and after the conversion sent to the data displaying module. The measurement of the above parameters were made in such a way, that after reaching maximum by the luminescence, two additional measurements of the luminescence intensity were made: $I_a$ for time $t_a$ and $I_b$ for time $t_b$, next the luminescence decay time was determined ($\tau$) as a difference quotient of the said measurement times ($t_b-t_a$) and the difference of the natural logarithms calculated during those luminescence intensity times ($\ln I_a-\ln I_b$) and in addition, one calculated the luminescence amplitude excited by drawing through the two above-mentioned points a straight line, which intersection point with the line parallel to the axis InI crossing the point $t_0$ (LED flash point) determined the exact $I_0$ level (or other fixed value in accordance with calibration table formation), which is dependent on the initial oxygen amount in $ZrO_2$. This value was compared with the value in the calibration table I-f (oxygen pressure) in the given temperature and the partial pressure of oxygen was obtained. The sensor temperature was determined as a quotient of the thermal energy of the luminescence activation decay ($E_a$) by the product of the Boltzmann constant (k) and the difference of the natural algorithm of the calibration parameter $\tau_0$ and the natural algorithm of the luminescence decay time determined earlier ($\tau$).

Another excitation pulses were switched on after the time equal to the sum of the excitation pulses ending times ($t_2$) and the quadruple of the luminescence time decay ($t_3-t_2$).

The sensitivity of the sensor, according to the invention, is below 1%, and the response time 100 μs. According to the invention, a method can be used for monitoring the partial pressure of oxygen in the analysed gas in the measuring range from 1% to 27%.

Obviously, the described above and shown on drawings embodiments of the present invention are only examples and it will be understood that this does not exhaust the spirit and scope of the present invention as defined by the following claims.

The invention claimed is:

1. Method of measuring partial pressure oxygen in gases by exciting luminescence of a sensor, characterised in that nanocrystalline zirconium dioxide in a calibrated sensor is contacted with a gas to be measured and is illuminated by a UV light impulse, which induces luminescence of the zirconium dioxide, then the luminescence intensity time dependence is being registered, the luminescence intensity of a pulse is being determined and the result obtained is compared with calibration results of the luminescence intensity as a function of the partial pressure of oxygen for the sensor temperature at a given time.

2. The method, according to claim 1, characterised in that the determined luminescence intensity equals maxima of luminescence response pulse.

3. The method, according to claim 1,
characterised in that the sensor contains nanocrystalline zirconium dioxide with crystallites from 3 nm to 200 nm made of monoclinic phase, doped tetragonal phase, regular doped phase or the mixture of those phases.

4. The method, according to claim 3, characterised by that the zirconia contains ions known to stabilise the monoclinic, tetragonal or regular phases or their mixtures.

5. The method, according to claim 3,
characterised by that the zirconia contains ions of rare and transition metals, which improve the sensitivity of the sensor and decrease the operating temperature.

6. The method, according to claim 1,
characterised in that when the temperature of the measured gas is below 100° C., the sensor is heated to a temperature in the range of 100° C. to 900° C. and the sensor working temperature is proportional to the size of the nanocrystalline grains.

7. The method, according to
claim 1, characterised in that the wavelength of the inducing excitation light impulse is within the range from 210 nm to 620 nm.

8. The method, according to claim 1, characterised in that the measuring of the sensor temperature at a given time is made on the basis of the exponent of the exponential function describing the luminescence decay as well as comparing the obtained value with the calibration results determining the connection between the temperature and this exponent.

9. The method, according to claim 1, characterised in that the measuring of the sensor temperature at a
given time is made on the basis of the rate of decay of luminescence, which is characteristic for the given material used in the sensor.

10. The method, according to claim 1, characterised in that the determined luminescence intensity equals any fixed level of luminescence response pulse which is lover than maximum level.

11. The method, according to claim 10, characterised in that the sensor contains nanocrystalline zirconium dioxide with crystallites from 3 nm to 200 nm made of doped monoclinic phase, tetragonal phase, regular phase or the mixture of those phases.

12. The method, according to claim 10,
characterised in that when the temperature of the measured gas is below 100° C., the sensor, is heated to a temperature in the range of 100° C. to 900° C. and the sensor working temperature is proportional to the size of the nanocrystalline grains.

13. The method, according to claim 10, characterised in that the wavelength of the inducing excitation light impulse is within the range from 210 nm to 620 nm.

14. The method, according to claim 10, characterised in that the measuring of the sensor temperature at a given time is made on the basis of the exponent of the exponential function describing the luminescence decay as well as comparing the obtained value with the calibration results determining the connection between the temperature and this exponent.

15. A method of measuring partial pressure oxygen in gases by exciting luminescence of a sensor
placing nanocrystalline zirconium dioxide in a calibrated sensor;
contacting the nanocrystalline zirconium dioxide with a gas to be measured;
illuminating the nanocrystalline zirconium dioxide by a UV light impulse;
inducing luminescence of the nanocrystalline zirconium dioxide with the UV light impulse registering a luminescence intensity time dependence;
determining the luminescence intensity of a pulse for obtaining a result;
comparing the result obtained with calibration results of the luminescence intensity as a function of a partial pressure of oxygen for the sensor temperature measured at a given time.

* * * * *